US007260857B2

(12) United States Patent
Cazzini et al.

(10) Patent No.: US 7,260,857 B2
(45) Date of Patent: Aug. 28, 2007

(54) CONFORMABLE BLANKET

(75) Inventors: Karl Hans Cazzini, Orchard Park, NY (US); Joel T. Jusiak, Holland, NY (US)

(73) Assignee: Gaymar Industries, Inc, Orchard Park, NY (US)

(*) Notice: Subject to any disclaimer, the term of this patent is extended or adjusted under 35 U.S.C. 154(b) by 57 days.

(21) Appl. No.: 11/037,067

(22) Filed: Jan. 17, 2005

(65) Prior Publication Data

US 2006/0156471 A1 Jul. 20, 2006

(51) Int. Cl.
*A47G 9/02* (2006.01)
*A47G 21/04* (2006.01)
*A61F 7/00* (2006.01)

(52) U.S. Cl. ....................... 5/482; 5/502; 5/423; 5/941; 219/212

(58) Field of Classification Search .................... 5/482, 5/485, 495, 502, 421, 423, 284, 941; 219/211, 219/212, 217, 529, 549
See application file for complete search history.

(56) References Cited

U.S. PATENT DOCUMENTS

| | | | | |
|---|---|---|---|---|
| 4,982,465 | A * | 1/1991 | Nagata et al. | 5/676 |
| 5,628,069 | A * | 5/1997 | Ebert | 2/161.1 |
| 5,873,768 | A * | 2/1999 | Fleischman-Ament et al. | 450/19 |
| 5,906,004 | A * | 5/1999 | Lebby et al. | 2/1 |
| 5,953,773 | A * | 9/1999 | Asada et al. | 5/81.1 R |
| 5,960,479 | A * | 10/1999 | Tamai | 2/268 |
| 5,974,588 | A * | 11/1999 | Furman | 2/159 |
| 2002/0078492 | A1* | 6/2002 | Gough et al. | 2/252 |
| 2003/0106127 | A1* | 6/2003 | Shwartz et al. | 2/12 |
| 2006/0090233 | A1* | 5/2006 | Botcher | 2/2.5 |
| 2006/0156471 | A1* | 7/2006 | Cazzini et al. | 5/482 |

* cited by examiner

*Primary Examiner*—Robert G. Santos
(74) *Attorney, Agent, or Firm*—Roach Brown McCarthy & Gruber, P.C.; Kevin D. McCarthy

(57) ABSTRACT

The present invention is directed to a blanket having at least one snap stick inserted into or onto the blanket to maximize the surface area of the blanket that contacts the user.

17 Claims, 2 Drawing Sheets

CONFORMABLE BLANKET

FIELD OF THE INVENTION

The present invention is directed to a blanket-like product that can cover a user.

BACKGROUND OF THE INVENTION

There are numerous types of blankets. There are conventional wool, fleece, cotton, flannel, down and electrical thermal blankets. These blankets can be purchased where bedding and/or blankets are sold. These blankets are also referred to as conventional blankets.

Other types of blankets include convective blankets. Since 1992, Gaymar manufactures and sells convective warming blankets to prevent or treat hyper/hypothermia. Gaymar's blankets feature an inflatable quilt-like structure. The blankets attach two sheets of the same amount of flexible, lightweight material around their periphery and at various spots along their surfaces. In operation, heated air flows onto a patient's body from holes in the undersurface of Gaymar's blankets, but the blankets do not form a self-supporting or Quonset hut-like structure. Instead, Gaymar's blankets lie flat when inflated on a flat surface and rest substantially on a patient when in use.

Other blankets receive a fluid and the fluid circulates through and out of the blanket through conduits. Examples of these blankets include and are not limited to Gaymar's DHP 600 Series Hyper/Hypothermia blanket, DHL520 Rapr Round Blanket and T-pads. These blankets are similar to the convective blankets except there are no holes in the undersurface. Instead, the fluid traverses through a path defined by areas where the two sheets are joined together. Once the entire fluid circulates through the path, the fluid is released through an outlet to a conduit. Hereinafter, such blankets are referred to as fluid path blankets.

For this application, the term "blanket" by itself, refers to any of the above-identified blankets. If a particular type of blanket is identified, then that sentence and/or paragraph is limited to that particular blanket design.

A problem with the blankets is that the blankets can not be positioned below the user and simultaneously extend toward the opposite side of the user (that includes sides of the user) without adhesives. Adhesives and tape can occlude the flow of the fluid in the convective and fluid path blankets. Such occlusion can be deleterious to providing the desired thermal energy to certain parts of the opposite side of the user.

Another problem with using tape is that tape does not allow the user to easily reposition the blanket without subjecting the blanket to rips and tears.

Another problem with tape is that some patients have skin reactions to the tape and the adhesive of the tape.

These problems and others are solved by the present invention.

SUMMARY OF THE INVENTION

The present invention is directed to a blanket having at least one snap stick inserted into or onto the blanket to maximize the surface area of the blanket that contacts the user.

DETAILED DESCRIPTION OF THE PRESENT INVENTION

Figure 1:
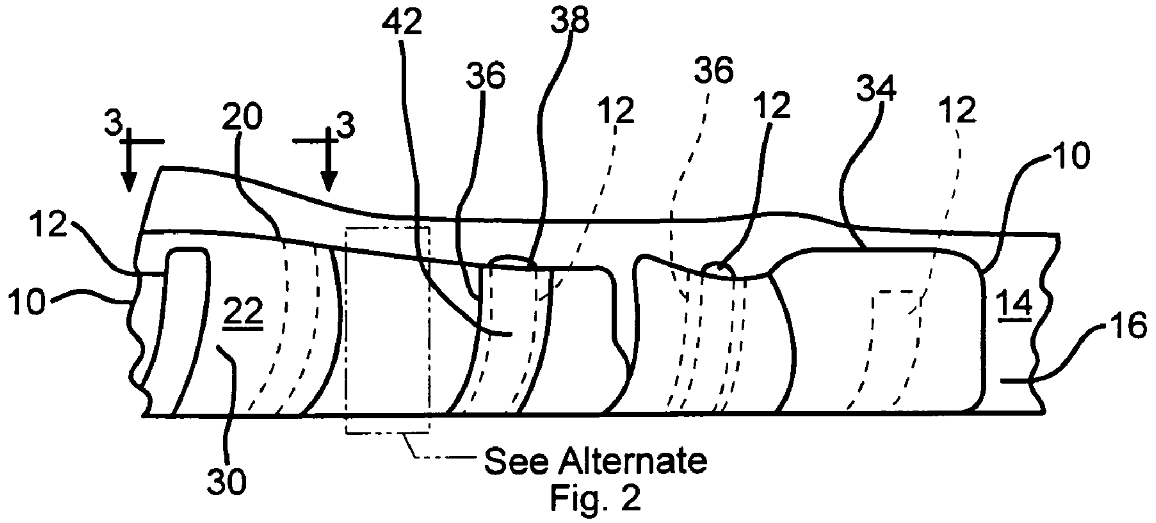
FIG. 1 illustrates an embodiment of the present invention.

The present invention utilizes a blanket 10 and at least one snap stick 12 inserted into or onto the blanket 10 to increase the surface area of the blanket 10 onto a user 14 if the blanket 10 is positioned below the user 14 as shown in FIG. 1.

The blanket 10 can be of any design, shape or size. Preferably, the blanket 10 is sized to fit under the user 14 with at least some additional surface area of the blanket 10 so the blanket 10 is able to extend beyond the side 16 of the user 14.

Starting at or near the perimeter 20 of the blanket 10 and protruding into the interior area 22 of the blanket 10 is at least one snap stick 12. A snap stick is a plastic, metal or bead like composition that can be shaped like a wire, a ribbon, or any other design that allows the blanket to maximize contact with the user. An example of the metal material is nitinol.

Nitinol is an alloy of nickel and titanium that belongs to a class of materials called shaped memory alloys (SMA). SMA's have interesting mechanical properties. Nitinol for example contracts when heated, which is the opposite of what standard metals do when heated (expand). Not only does the alloy contract, but also it produces a 100 times greater thermal movement (expansion, contraction) than standard metals.

A shape memory alloy is capable of remembering a previously memorized shape. It has to be deformed in its low temperature phase Martensite and subsequently heated to the high temperature phase Austenite, e.g., in hot water or with an electrical current. The alloy generates a high force during the phase transformation. Thus, it can be used as an actuator in a multitude of different applications. The shape change is not restricted to just pure bending. The most suitable actuation mode has proved to be the linear contraction of a straight wire actuator.

Nitinol ribbon is supplied in different alloys, widths and thicknesses, treatment conditions and surfaces. Nitinol ribbon is available in different alloy compositions, some of which are superelastic materials and others are used as actuator materials.

Nitinol is used in a vast variety of applications in medical implants and instruments. It has excellent corrosion behavior.

Figure 4:
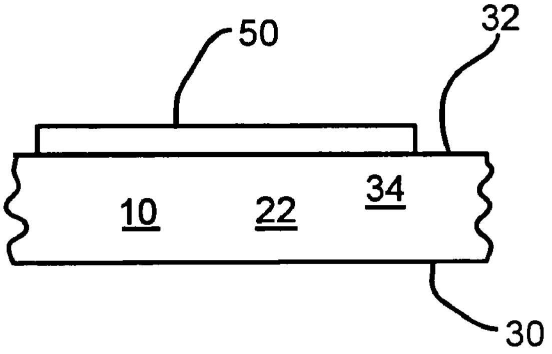
FIG. 4 is a top-side alternative embodiment of FIG. 1.
Figure 5:
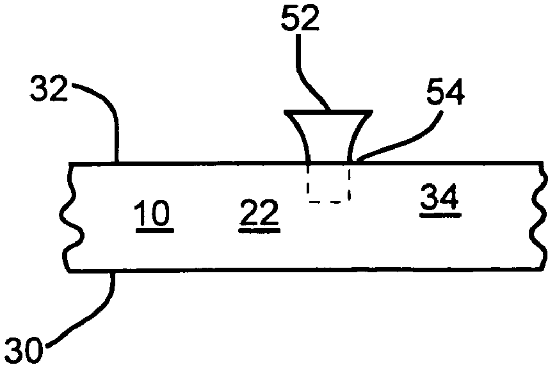
FIG. 5 is a top-side alternative embodiment of FIG. 1.

Reverting to FIGS. 1, 4 and 5, the snap stick 12 is positioned on the exterior outside surface 30, the exterior inside surface 32, within the interior surface 34 of the blanket 10, and/or within a packet 36 positioned on at least one exterior surface and/or that protrudes into the interior surface.

If a packet 36 is used, the packet 36 can have at least one opening 38. The opening 38 is positioned at and/or near a perimeter 20 of the blanket 10. The packet 36 is also attached to an interior and/or exterior surface 30, 32, 34 of the blanket 10 by conventional methods. Conventional methods include and are not limited to welding, adhesives, sewing, sonic welding, melting, and combinations thereof.

In the embodiment illustrated in FIG. 1, the packet is securely attached to the blanket 10 to form a conduit 42 in conjunction with the opening 38 that allows the snap stick 12 to enter the opening 38 and contact the blanket 10. Once the snap stick 12 contacts the blanket 10, the snap stick 12 can be activated to have the blanket 10 conform to at least a part of the shape of the user. When the blanket 10 conforms to the shape, or at least a part of the shape, of the user, the blanket 10 has increased surface area on the user. Increased surface area means the blanket is providing the desired thermal energy transfer and/or maintenance to the user.

The snap stick 12 can be positioned entirely within the conduit 42 and extending from the conduit 42. The desired distance of the snap stick 12 entering the conduit is dependent upon how much of the blanket 10 will contact the user.

Alternatively, the packet need not have an opening so the snap stick is contained within the packet area.

If a packet 36 is not being used, the snap stick 12 is attached to the blanket 10 by the same conventional methods that the packet 36 is attached to the blanket 10.

It is desired that the snap sticks 12 be utilized in association with the convective and fluid flow blanket designs. Those blankets have thermal energy traverse through the blankets. The snap sticks 12, if a thermoplastic material and/or a metallic material, should preferably allow thermal energy to pass there through to the user.

Alternatively, the blanket 10 can have an insulation layer 50 on the exterior surface 30 and/or the exterior surface, 32 as illustrated in part in FIG. 4. The insulation layer can be any conventional insulation material that can be directly applied to a user's skin and/or clothing. The insulation conserves energy and reduces pressure to the user.

Alternatively, the blanket 10 can have a conductive material 52 as illustrated in FIG. 5. Examples of conductive material 52 include metallic sheets interspaced throughout the blanket 10 as illustrated by expired U.S. Pat. No. 4,846,176, or the metallic sheets can be substituted with rivet-like designs. The rivet-like designs would use a significantly decreased aperture 54 that holds the metallic sheets illustrated in the '176 patent. The decreased aperture size would decrease the quantity of fluid leakage if the blanket was a convective and/or fluid flow blanket. To secure the conductive material in place, conventional securing devices or method, like clips or crimping can be used with the conductive material in relation to the blanket. The use of the conductive material promotes the efficient transfer of the fluid's thermal energy from within the blanket to the user through the conductive material.

Figure 2:
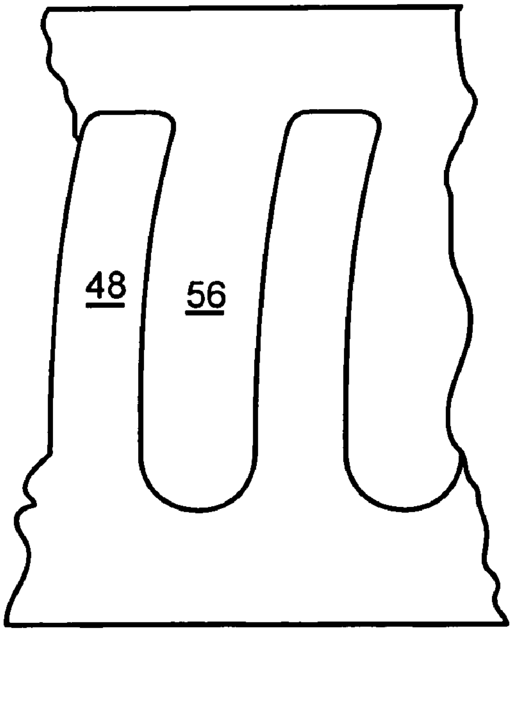
FIG. 2 illustrates an alternative embodiment of FIG. 1 at box 2.

The present invention can also be used in a blanket that combines a convective blanket and a fluid flow blanket, or combinations with other blanket types. Each portion of the blanket can be one part of an alternating pressure support system. An example of such an alternating support system is disclosed and illustrated in U.S. Pat. No. 5,901,393, which is commonly assigned and hereby incorporated by reference herein. For example, we refer to FIG. 1 of the '393 patent and FIG. 2 of the present invention wherein finger cells 48 and the coordinated system can contain convective blanket characteristics, and finger cells 56 and its coordinated system can contain a fluid flow blanket system.

Figure 3:
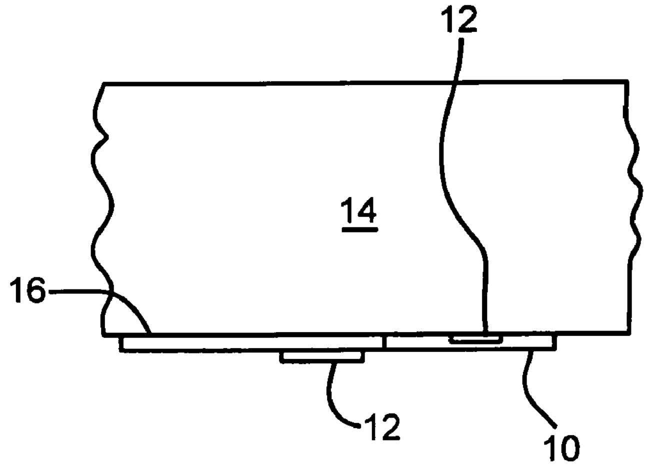
FIG. 3 is a top view of FIG. 1 taken from lines 3—3.

The present blanket 10 with at least one snap stick 12 automatically positions itself about the user when a fluid enters the blanket and when the blanket is a fluid flow blanket, a convective blanket or combination thereof. The blanket can be positioned above the user, below the user, and/or on the side of the user. The blanket contacts the user and with the snap sticks 12 ensures that the blanket 10 applies the maximum available surface area to the user without applying tape directly to the user as illustrated in FIGS. 1 and 3. It is preferred that the blanket 10 for certain operations not be positioned to contact the shoulders or cover the nipple or cover the inside of the legs. With the snap sticks 12, the blankets can be easily repositioned to have the blanket 10 positioned where desired for particular surgical procedures.

Although a particular preferred embodiment of the invention has been illustrated and described in detail for illustrative purposes, it will be recognized that variations or modifications of the disclosed apparatus, including the rearrangement of parts, lie within the scope of the invention defined by the claims.

The embodiments of the invention in which an exclusive property or privilege is claimed are defined as follows:

We claim:

1. A blanket comprising:

a blanket selected from the group consisting of a fluid flow blanket and a convective blanket;

wherein the blanket has at least one sheet that defines an interior cavity, the interior cavity receives a fluid that flows within the interior cavity and affects a patient's temperature, and when the fluid is within the interior cavity the fluid does not contact the patient; and at least one snap stick positioned on the exterior surface of the blanket to maximize the blanket's contact with the patient.

2. The blanket of claim 1 wherein at least one snap stick is attached to the exterior surface of the blanket.

3. The blanket of claim 1 wherein the blanket has a packet attached to the exterior surface of the blanket and the packet receives the at least one snap stick.

4. The blanket of claim 3 wherein the packet has an opening that allows the snap stick to be positioned within the packet.

5. The blanket of claim 1 wherein the convective blanket, has apertures that direct the fluid toward the patient when the fluid is not within the interior cavity.

6. The blanket of claim 1 wherein the blanket has insulation on the exterior surface.

7. The blanket of claim 1 wherein the exterior surface of the blanket is a conductive material.

8. A blanket comprising:

a blanket selected from the group consisting of a fluid flow blanket and a convective blanket;

wherein the blanket has at least one sheet that defines an interior cavity, the interior cavity receives a fluid that flows within the interior cavity and affects a patient's temperature, and when the fluid is within the interior cavity the fluid does not contact the patient; and at least one snap stick positioned on the interior surface of the blanket to maximize the blanket's contact with the patient.

9. The blanket of claim 8 wherein at least one snap stick is attached to the interior surface of the blanket.

10. The blanket of claim 8 wherein the blanket has a packet attached to the interior surface of the blanket and the packet receives the at least one snap stick.

11. The blanket of claim 10 wherein the packet has an opening that allows the snap stick to be positioned within the packet.

12. The blanket of claim 8 wherein the convective blanket, has apertures that direct the fluid toward the patient when the fluid is not within the interior cavity.

13. The blanket of claim 8 wherein the blanket has insulation on the exterior surface.

14. The blanket of claim 8 wherein the exterior surface of the blanket is a conductive material.

15. A blanket comprising:

a blanket and at least one snap stick positioned on the exterior surface of the blanket wherein the blanket is a fluid flow blanket and/or convective blanket and the fluid within the blanket contacts a conductive material that (1) penetrates into a cavity where the fluid circulates within the blanket, and (2) is exposed to the exterior surface of the blanket that is designed to contact the user so the conductive material transfers the thermal energy of the fluid through the conductive material to the user.

16. A blanket comprising:

a blanket and at least one snap stick positioned on the interior surface of the blanket wherein the blanket is a fluid flow blanket and/or convective blanket and the fluid within the blanket contacts a conductive material that (1) penetrates into a cavity where the fluid circulates within the blanket, and (2) is exposed to the exterior surface of the blanket that is designed to contact the user so the conductive material transfers the thermal energy of the fluid through the conductive material to the user.

17. A blanket comprising:

a blanket selected from the group consisting of a fluid flow blanket and a convective blanket;

wherein the blanket has at least one sheet that defines an interior cavity, the interior cavity receives a fluid that flows within the interior cavity and affects a patient's temperature, and when the fluid is within the interior cavity the fluid does not contact the patient; and at least one snap stick positioned within the interior cavity of the blanket to maximize the blanket's contact with the patient.

* * * * *